United States Patent
Hanoun

[19]

[11] Patent Number: 5,997,440
[45] Date of Patent: Dec. 7, 1999

[54] CERVICAL MUSCLE EVALUATION APPARATUS

[76] Inventor: Reed Hanoun, 50 Findlay Ave., King City, Ontario, Canada

[21] Appl. No.: 08/935,112

[22] Filed: Sep. 29, 1997

[51] Int. Cl.$^6$ .......................... A63B 23/025; A61B 5/103
[52] U.S. Cl. .......................... 482/10; 600/595; 600/594; 600/587
[58] Field of Search ................ 482/144, 10; 600/587, 600/594, 595

[56] References Cited

U.S. PATENT DOCUMENTS

| | | | |
|---|---|---|---|
| 4,066,259 | 1/1978 | Brentham | 482/10 |
| 4,278,249 | 7/1981 | Forrest | 482/10 |
| 4,492,236 | 1/1985 | Pile | 600/595 X |
| 4,655,450 | 4/1987 | Rogers | 482/10 |
| 4,768,779 | 9/1988 | Oehman | 482/10 |
| 4,845,987 | 7/1989 | Kenneth | 482/10 |
| 4,893,808 | 1/1990 | McIntyre | 482/10 X |
| 5,094,249 | 3/1992 | Marras | 600/595 X |
| 5,118,098 | 6/1992 | Jones | 482/10 |
| 5,474,086 | 12/1995 | McCormick | 600/595 |

*Primary Examiner*—Richard J. Apley
*Assistant Examiner*—William LaMarca

[57] ABSTRACT

A cervical muscle evaluation apparatus comprises a head station which is adjustable to different head sizes and shapes, a body positioning unit which positions the user's body for head placement in the head station and an indicator which indicates cervical muscle controlled head movement of the user's head within the head station.

7 Claims, 13 Drawing Sheets

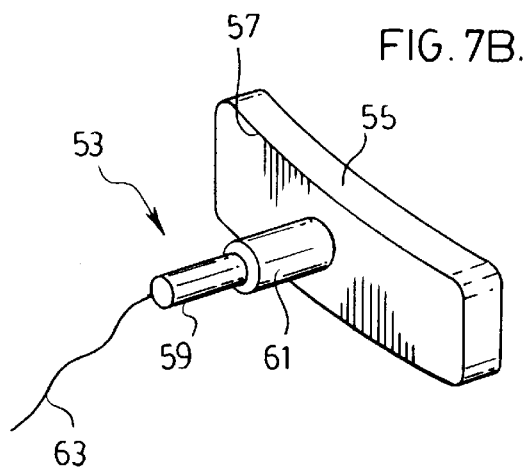
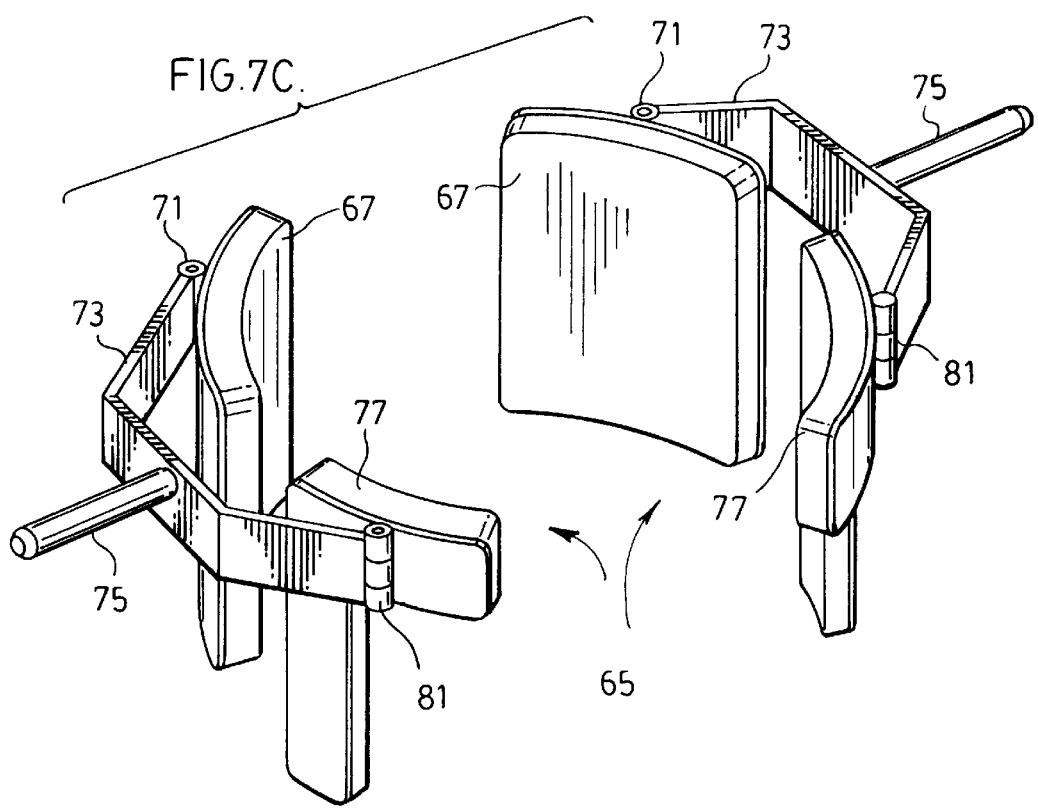

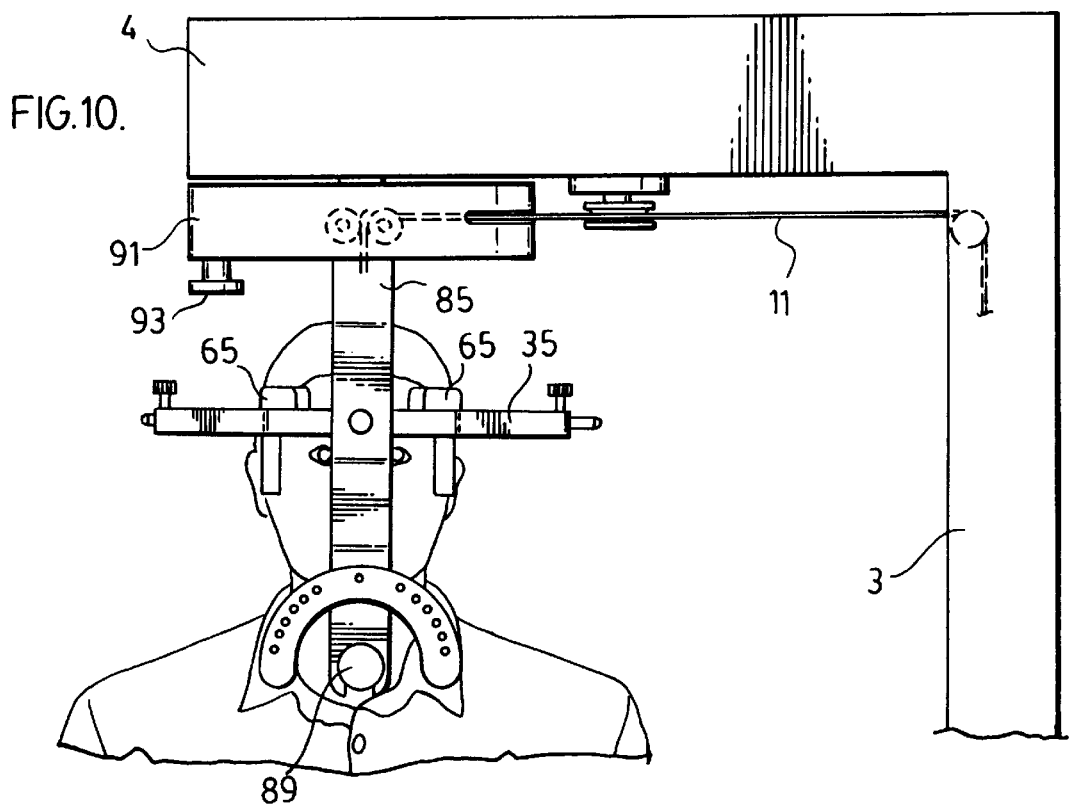
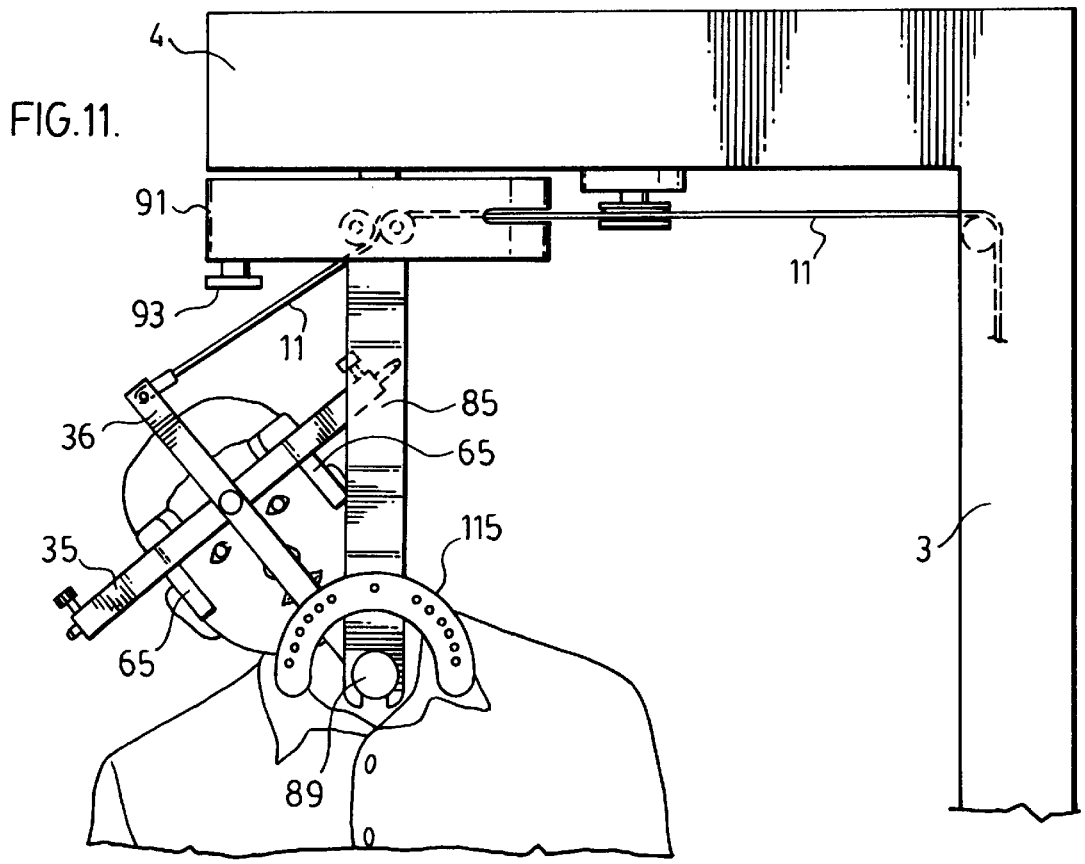

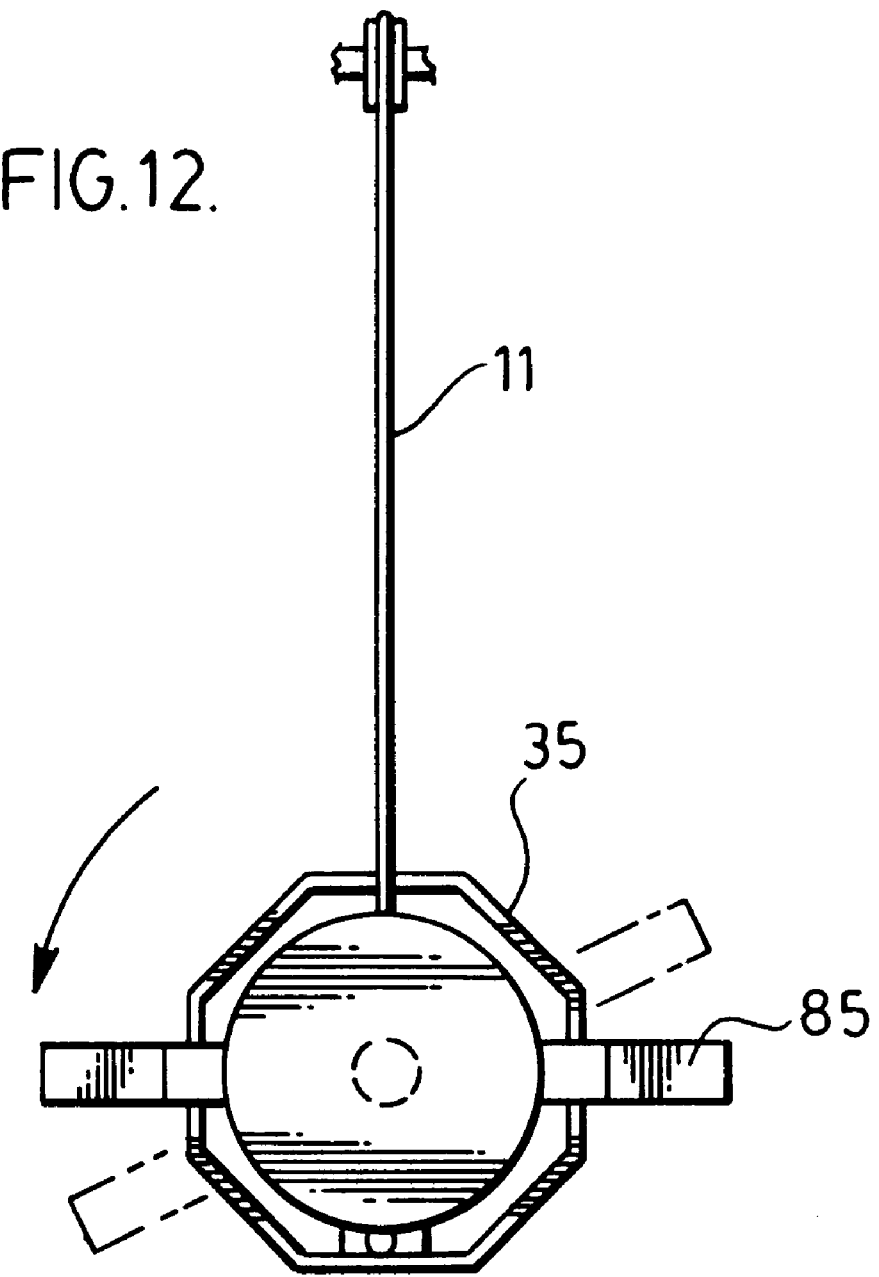

CERVICAL MUSCLE EVALUATION APPARATUS

FIELD OF THE INVENTION

The present invention relates to a cervical muscle evaluation and conditioning apparatus.

BACKGROUND OF THE INVENTION

Cervical injuries are among the most frequent and potentially debilitating of all injuries. Significant factors that contribute to this high incidence are chronic disuse, motor vehicle accidents and sports activities. It is difficult to deal with these injuries because cervical muscles are one of the least conditioned muscle groups due to a lack of conditioning devices and the fear of injury in performing cervical exercises.

Previous cervical training methods have been very inconsistent with very little, if any, quantification of the results of these methods. Past conditioning has been in the form of light stretching with some resistance either manually or by a free weight attached to the user by some type of harness or the like. More recently, chiropractic methods have been used which involve manipulation of the cervical region of a patient by the practitioner.

There is nothing presently available in a single apparatus with multi-direction movement capacity which can be used for both evaluation and conditioning while isolating specific muscles of a person suffering from a cervical injury. Furthermore, there is no current method of providing controlled progressive resistance training in the cervical region for treating injuries such as whiplash where a balance between flexion and extension need to be restored. Also, it is important to have a full range of flexion in combination with movements such as rotation and again there is nothing currently satisfactory to train these combination movements.

SUMMARY OF THE INVENTION

The present invention provides a cervical muscle evaluation apparatus which comprises a frame supporting a head station that is adjustable to different head sizes and shapes, a body positioning unit which positions the user's body for head placement in the head station and an indicator which indicates cervical muscle head movement at the head station while the user's body is stabilized at the body positioning unit.

The cervical muscle evaluation apparatus as described above is able to isolate the cervical muscle region for head movement within the apparatus and is further able to quantify the results of the head movement.

BRIEF DESCRIPTION OF THE DRAWINGS

The above as well as other advantages and features of the present invention will be described in greater detail according to the preferred embodiments of the present invention in which;

FIG. 7b is a perspective view of a load cell fittable with the head brace of FIG. 7;

FIG. 7c is a perspective view of an alternate set of head pads usable with the head brace of FIG. 7;

FIGS. 8 through 14 show user operation of the apparatus of FIG. 1;

DETAILED DESCRIPTION ACCORDING TO THE PREFERRED EMBODIMENTS OF THE PRESENT INVENTION

Figure 1:
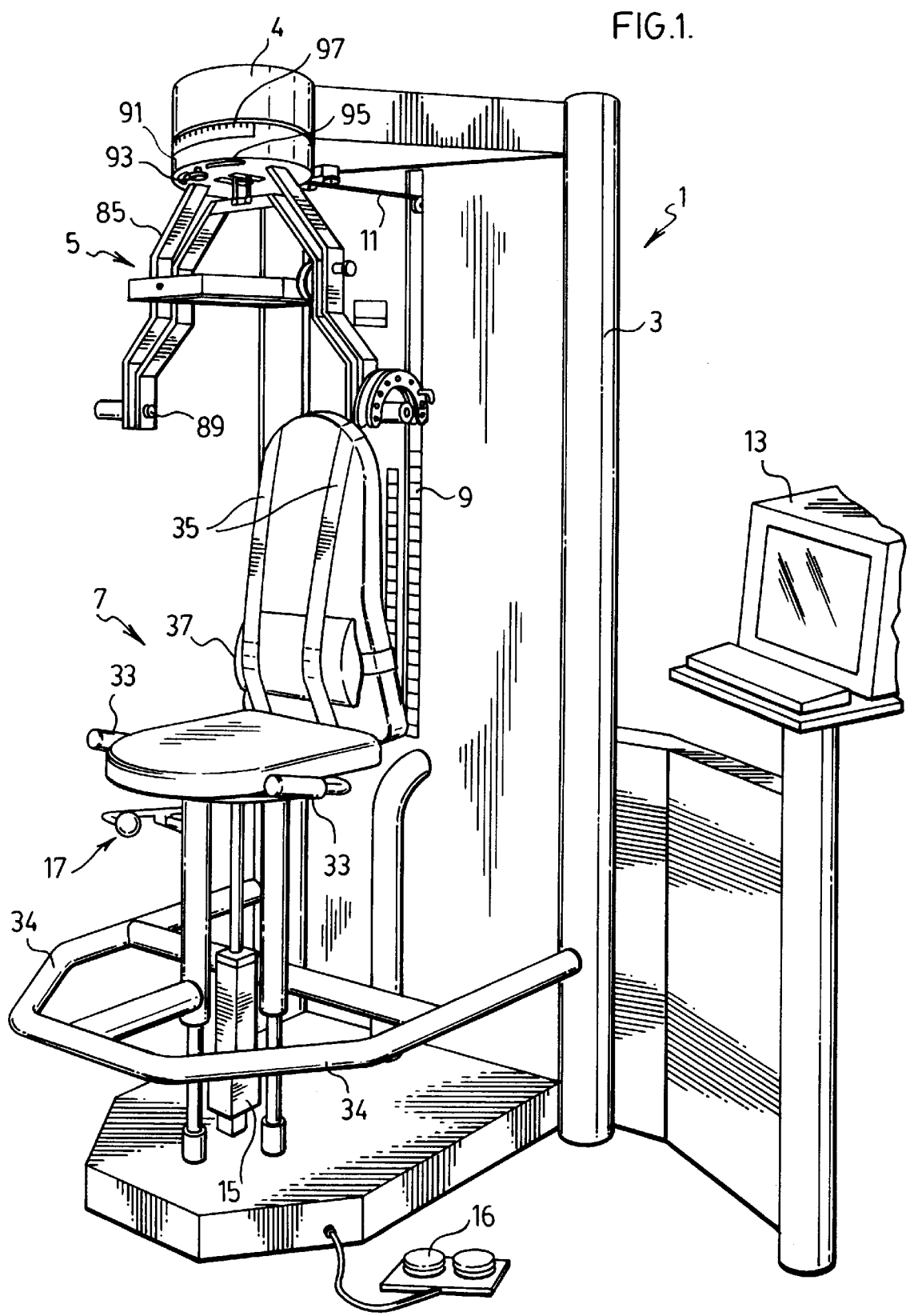
FIG. 1 is a perspective view of a cervical muscle evaluation and training apparatus according to a preferred embodiment of the present invention.

FIG. 1 shows a cervical muscle evaluation and training apparatus generally indicated at 1. This apparatus comprises a frame 3 supporting a head station 5, a seating unit 7 below the head station and a weight stack 9 behind the seating unit. The weight stack is connected to the head station by means of a cable 11.

Seating unit 7 is height adjustable relative to the head station by means of an electronic lifting cylinder 15 which is controlled by an electronic foot pad 16. The foot pad as shown has up and down contact switch pressure pads which will raise and lower the seating unit either with or without the user of the apparatus sitting on the seating unit.

As will be appreciated, foot control 16 can easily be replaced by some other type of control such as a hand operated control situated directly on the apparatus.

Figure 4:
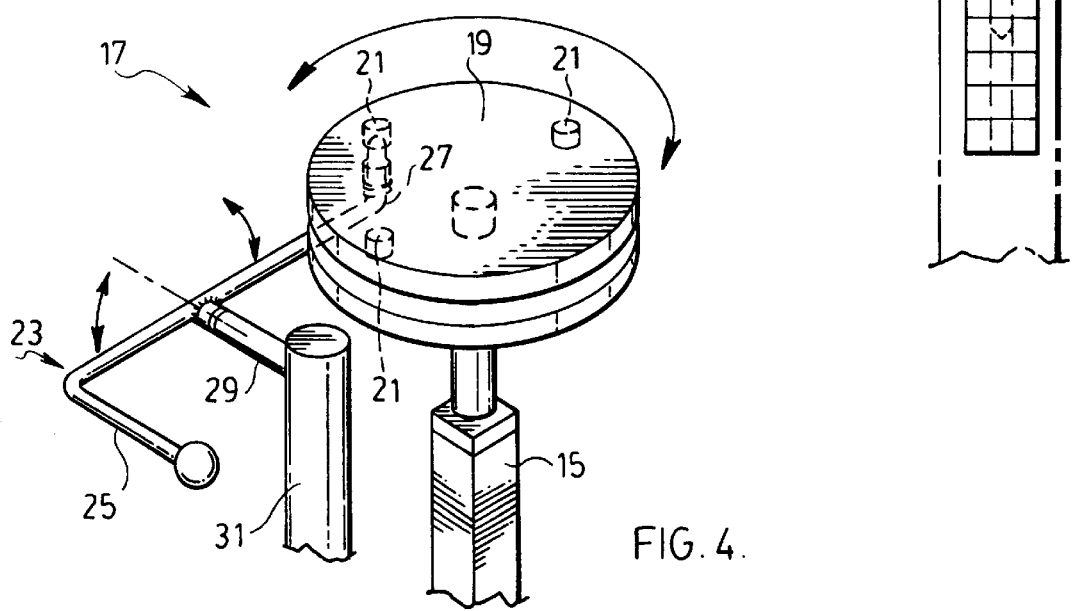
FIG. 4 is a perspective view of the seat control for adjusting rotational position of the seating unit of the apparatus of FIG. 1.

The seating unit is also rotatable relative to the head station through the use of a rotation control mechanism generally indicated at 17 and better shown in FIG. 4 of the drawings. This rotation control mechanism comprises a plate 19 rotationally coupled to the lift cylinder 15 and secured to the undersurface of the seating unit. The base of the plate is provided with spaced apart openings 21 at 90° to one another peripherally of the plate. A lever generally indicated at 23 is secured by a pivot mount 29 to a support post 31. This lever has a control handle 25 at one end of the lever and an upwardly bent end portion 27 at the other end of the lever.

When the handle portion 25 of the lever is pulled upwardly, the end portion 27 is drawn downwardly away from plate 19. In this position, the seating unit is allowed to rotate. The lever, when released, is spring loaded to assume the FIG. 4 position such that the end portion 27 of the lever moves up and locks into the appropriate opening 21 in the plate according to the positioning of the seating unit.

In the arrangement shown in FIG. 4, the plate is provided with three openings 21 which allows for a forward positioning of the seating unit as shown in FIG. 1 and a rotation of the seating unit 90 to either side of the forward positioning. As will be appreciated, additional openings could be provided in the plate for incremental rotation of the seating unit between these three positions.

The purpose of rotating the seating unit will be described later in detail.

Seating unit 7 is specifically designed to stabilize the user of the apparatus beneath the head station. This is achieved through the provision of a pair of shoulder restraints 35 which can be adjusted tightly to the user. A lumbar support 37 is adjustably fitted to the back rest of the seating unit and acts in cooperation with the shoulder restraints for a comfortable yet tight fitting of the seating unit to the back of the user. Hand grips 33 are provided to either side of the seating unit while a foot rest 34 is provided below the seating unit. A user of the apparatus is able to increase his or her leverage by pushing down on the foot rest while pulling upwardly on the hand grips. This, in combination with the secured holding of the user's torso on the seating unit, effectively isolates head movement to the use of the muscles in the cervical region of the user.

The head unit itself is movable in a number of different manners including both tilting and rotation of the head station. These movements are monitored by electronic sensors in the apparatus such as sensor 14 shown in FIG. 2 and the output of those sensors is shown on a visual display, in this case a monitor 13 as shown in FIG. 1. Accordingly, movements such as range of motion for muscle flexion, extension and rotation can be easily evaluated. Furthermore, as a result of a unique double pivoting action of the head station, evaluations can also be made relative to cervical protraction and retraction. These movements will all be described in detail with respect to FIGS. 8 through 14 of the drawings.

The movement sensors used are preferably of a potentiometer type where a certain voltage is fed to the input side of the sensor which senses movement of the cable and the voltage emitted from the sensor is dependent upon the amount of movement of the cable.

Head station 5 will now be described having particular reference to FIGS. 2 and 7 through 7c of the drawings. This head station comprises an inner head brace which is pivotally attached at pivot points 89 to an outer head unit 85. The inner head brace comprises a first frame piece 35 secured by pivot connections 37 at either side of the frame piece to a second frame piece 36. Collars 38 surrounding the pivot connections 37 are fixedly secured to the frame piece 36. Each of these collars is provided with an opening 40 to receive a releasable pin 42. A plurality of openings 37a are provided in the pivot connections 37 which in combination with openings 40 and pin 42 provide different angled settings of the frame pieces 35 and 36 relative to one another for reasons to be described later in detail.

The frame piece 35 of the inner head brace is provided with a pair of adjustable openings 39 facing one another and at 90° to the pivot connection between frame pieces 35 and 36. Each of these adjustable openings includes a manual adjustment member 41.

Figure 7:
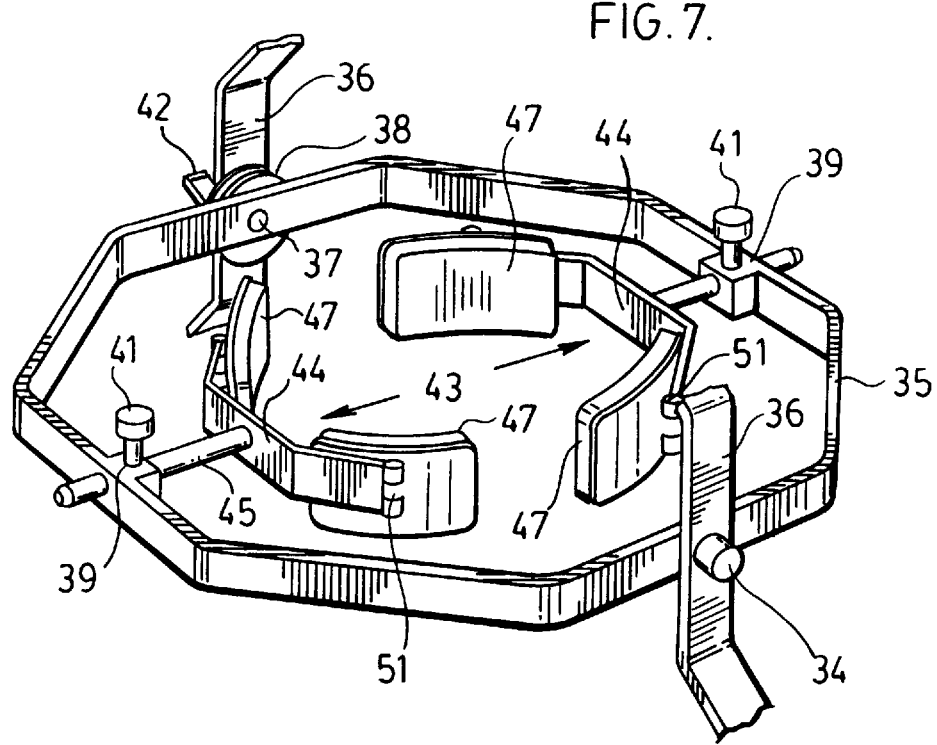
FIG. 7 is a perspective view of the inner head brace of the head station from the apparatus of FIG. 1.

In the set up shown in FIG. 7, a pair of head pads generally indicated at 43 are secured by their stems 45 in the openings 39 of the inner head brace. Adjustment members 41 tighten down onto the stems after the head pads have been appropriately fitted to a user of the apparatus.

Each of the head pads 43 includes a base portion 44 to which the stem 45 is secured and a pair of pad members 47 pivotally secured at 51 to the base member 44. The head pads 43 are adjusted inwardly and outwardly to one another along their stems 45 for head size adjustment while the pads 47 automatically align themselves to the shape of the user's head.

Figure 8:
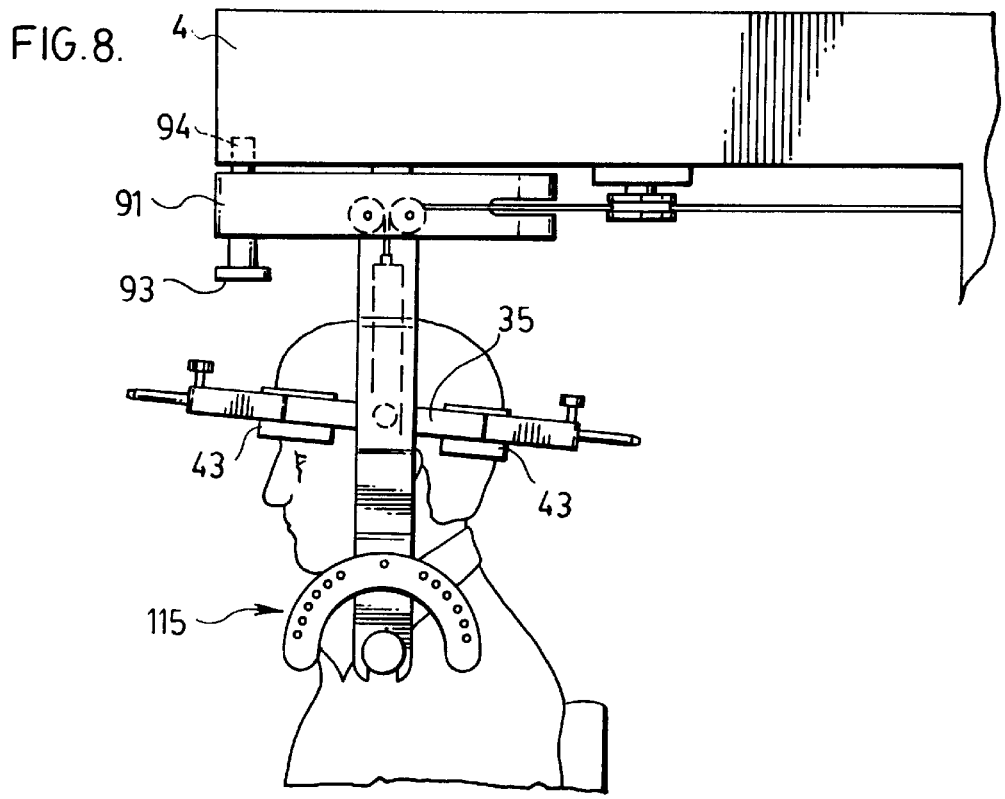

The head brace as shown in FIG. 7 using the pads 43 is set up to fit with a person sitting in a forwardly facing position on the apparatus as shown for example in FIG. 8 of the drawings.

Many different types of cervical muscle controlled head movements can be achieved with the head station. However, it is also possible to completely lock the head station against any movement and to replace either one of the pads 43 with a load cell generally indicated at 53 in FIG. 7b. This load cell includes a stem 59 substantially the same as stem 45 on pad 43 and a pad portion 55. A pressure sensor 61 is provided immediately behind the pad 55. This pressure sensor produces an output fed along electrical lines 63 to the visual readout 13 of the apparatus.

When it is desired to determine cervical muscle strength rather than range of motion, the head unit as described above is preferably locked in a stationary position and one of the pads 43 is replaced by the load sensor 53. The user of the apparatus then pushes his or her head onto the load sensor which determines the amount of force or exertion being used and feeds that information to the visual display.

If desired, load sensors can be used in replacement of both of the pads 43 to measure both forward and rearward muscle strength.

FIG. 7c shows a pair of head pads 65 which are used in replacement of the pads 43 when the user of the apparatus rotates the seating unit and sits in a sideways position as shown in FIG. 10 of the drawings. These pads 65 comprise a base plate 73 provided with a stem 75 and first and second pad members 67 and 77 respectively. The pad members 67 are pivotally secured at 71 to the base plate 73 while the pad members 77 which are generally L shaped are pivotally connected at 81 to the base plate 73.

When the user is seated sideways as shown in FIG. 10 of the drawings, the larger pads 67 fit to the rear while the smaller L-shaped pads fit to the front of the user's head. Again, both sets of pads float on the pad frames to alight with the shape of the user's head while the pads are adjustable towards and away from one another along their stems 75 for accommodating different head sizes.

As earlier described, the head station can be fixed against movement when used, for example, in evaluation of muscle strength with a load cell. In order to do this, the inner head brace may be locked with the outer head unit which is supported against tilting movement by the frame of the apparatus as clearly seen in FIG. 1 of the drawings. The outer head unit can be rotated as to be described later in detail, but also can be locked against rotation.

Figure 7A:
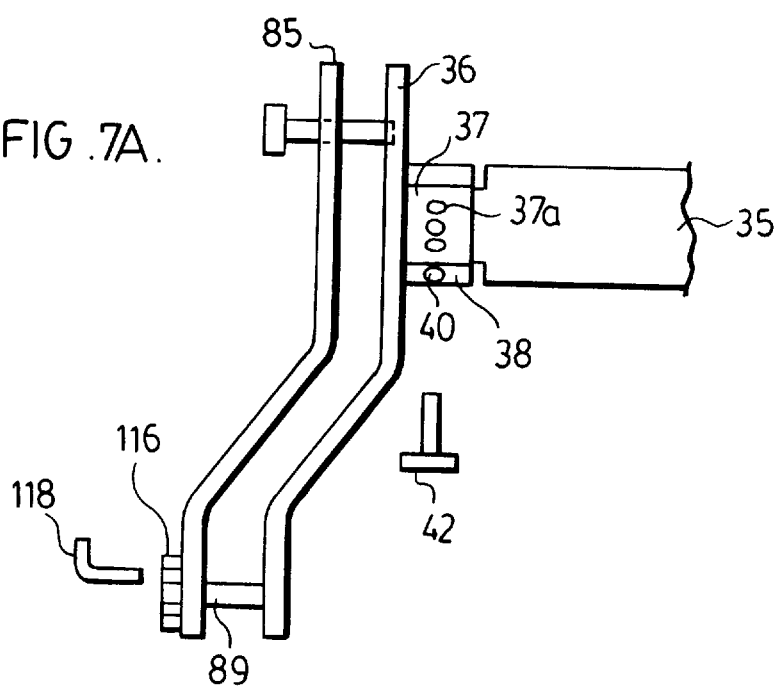
FIG. 7a is an enlarged sectional view of one side of the inner head brace of FIG. 7.

FIG. 7a shows the lower pivot connection 89 between the inner head brace and the outer head unit. FIG. 7a also shows the provision of a releasable lock pin 87 which extends through the outer head unit 85 into the frame member 36 of the inner head brace. When the lock pin is in the FIG. 7a position, the inner head brace is locked against pivotal movement relative to the outer head unit and as described above, the outer head unit itself is locked against any rotational movement thereby making the head station completely immobile.

Figure 2:
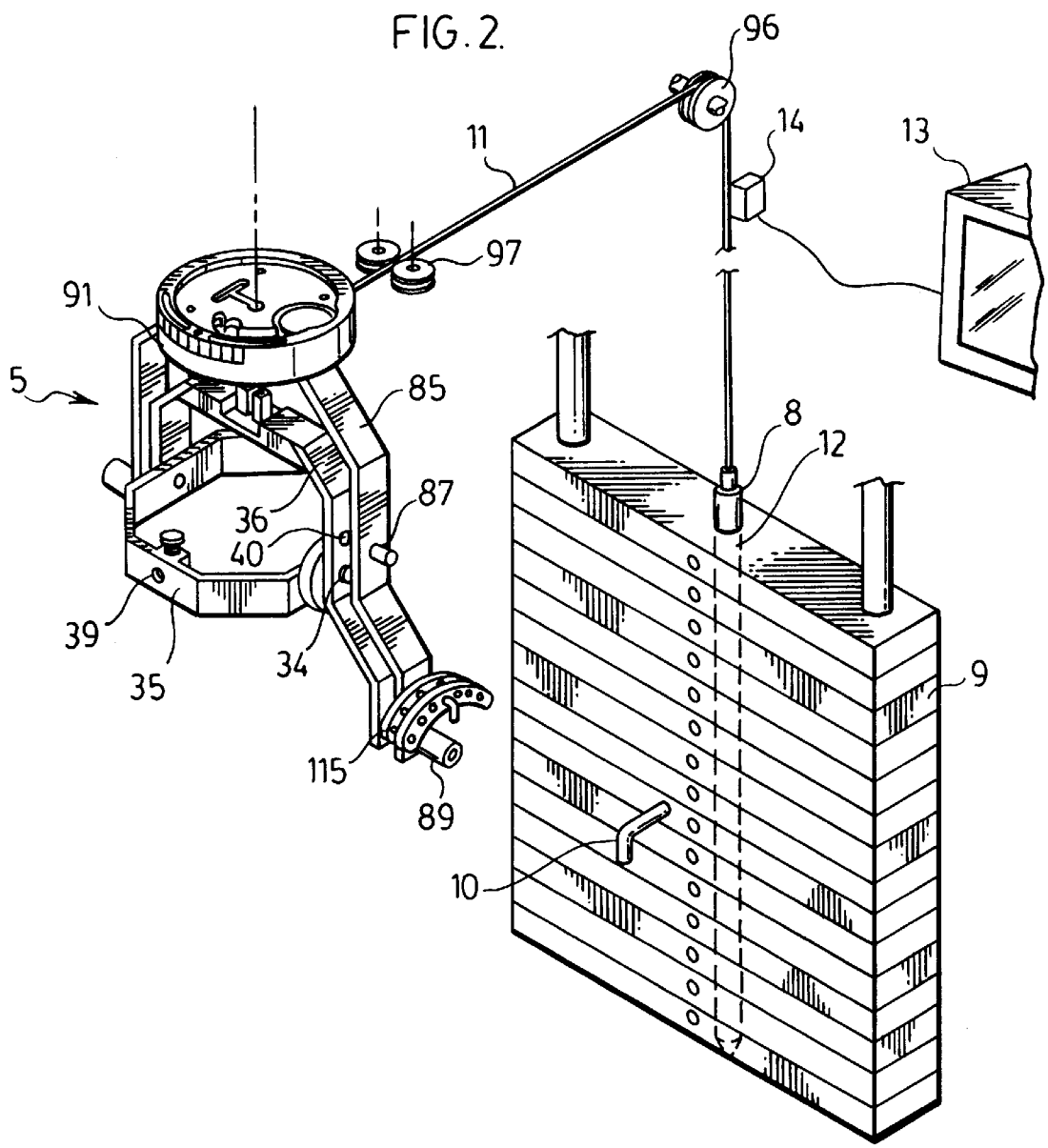
FIG. 2 is a perspective view of the head station and weight stack from the apparatus of FIG. 1.
Figure 5:
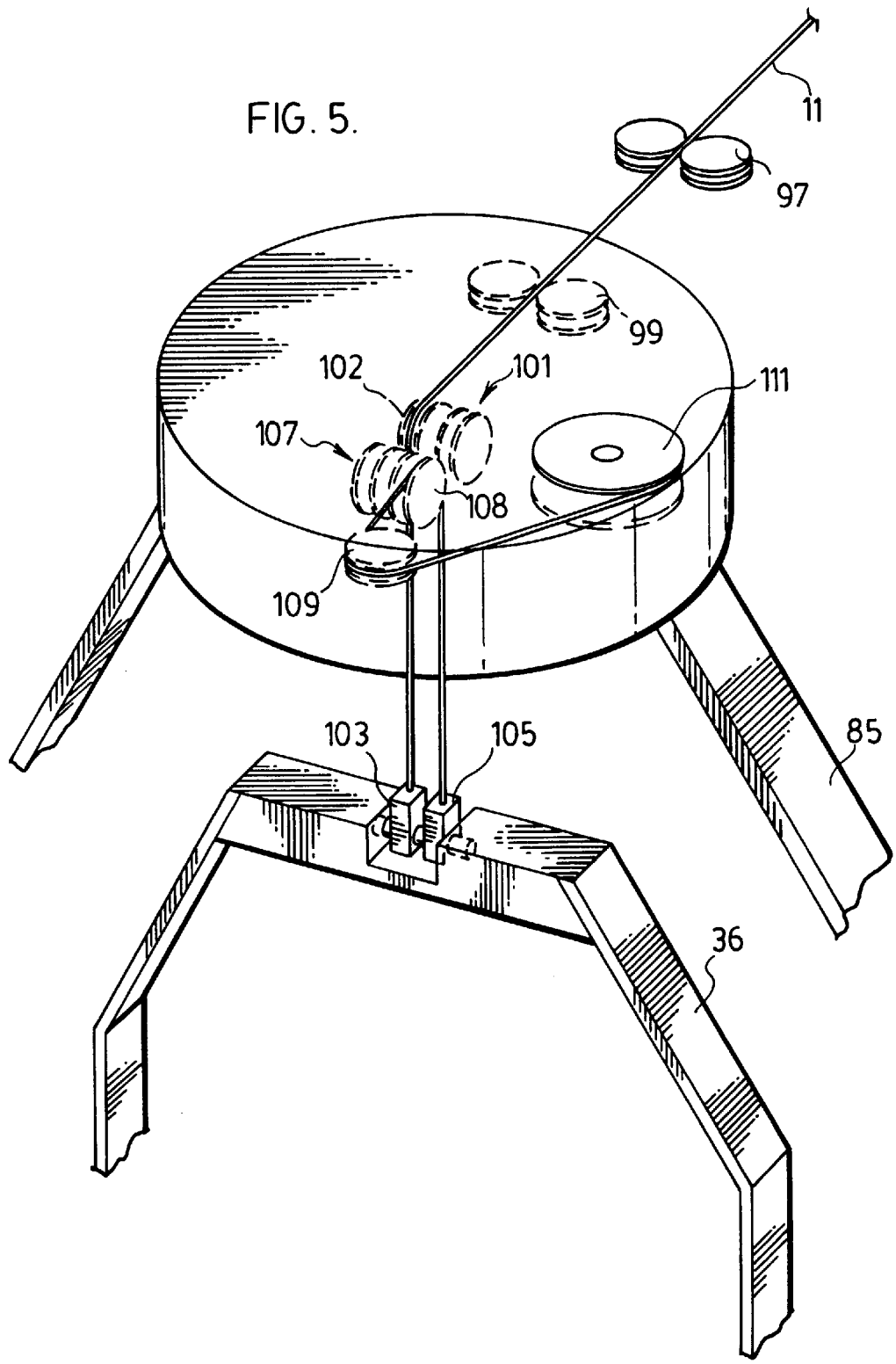
FIG. 5 is an enlarged assembled perspective view of the upper region of the head station of the apparatus of FIG. 1.
Figure 6:
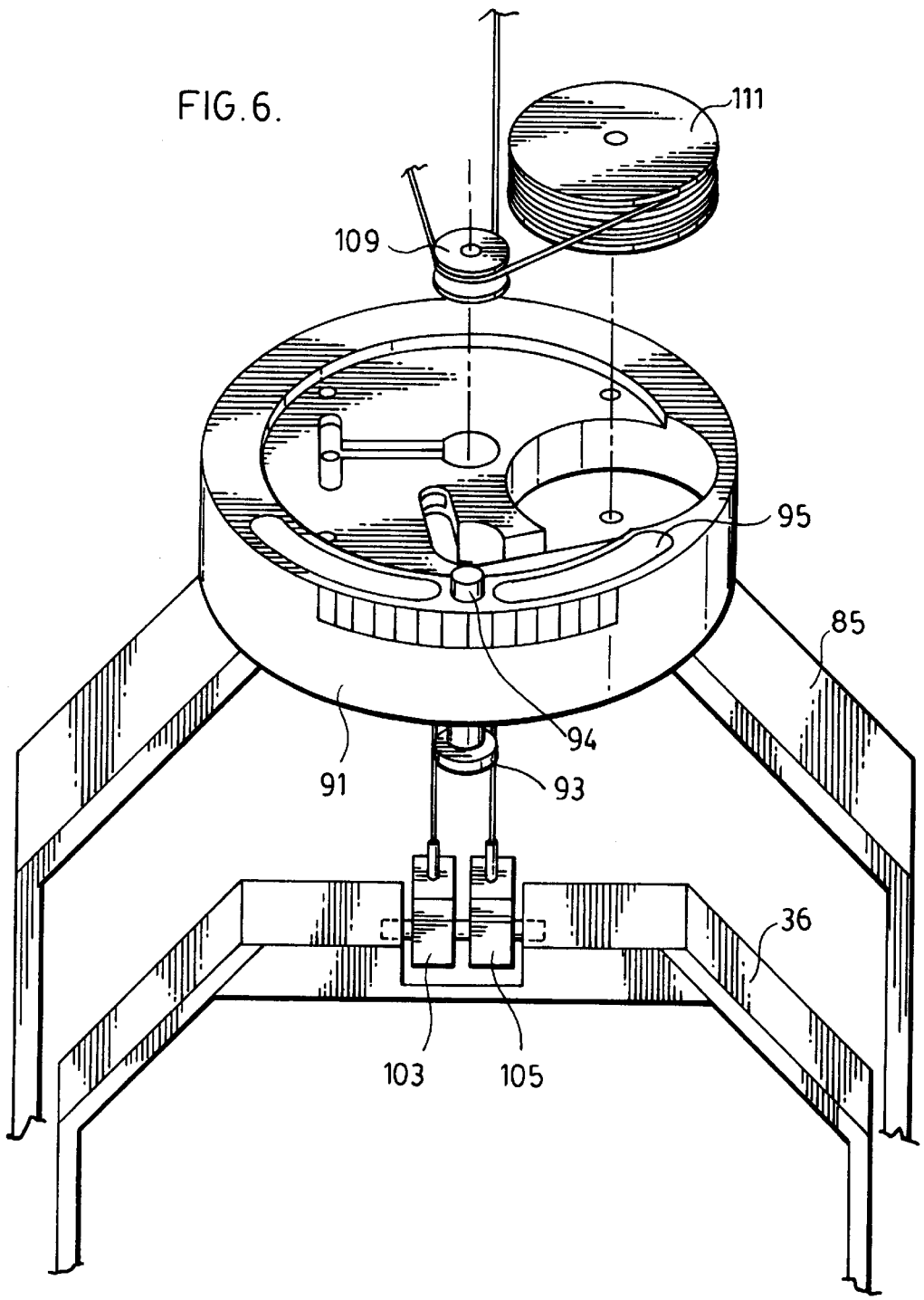
FIG. 6 is an enlarged partially exploded perspective view of the head station of the apparatus of FIG. 1.

Before describing specific head movements as shown in FIGS. 8 through 14, reference should be made to FIGS. 2, 5 and 6 of the drawings which show the cable connection of the head unit to the weight stack 9. FIG. 2 shows that the cable 11 is secured to a bar 12 extending down through the weight stack and having an opening aligned with each of the individual weight plates. The pin 10 fits through the particular weight plate selected and then into bar 12 and that weight plate, plus any plate above it is lifted by the bar through a movement of the head station.

Also provided is a force sensor 8 which gives a more accurate reading of the amount of weight lifted. the positioning of pin 10 gives an approximate idea of the weight but due to the lever effect of the pulleys in the apparatus which are described below the actual weight varies according to the position of the head unit. The force sensor is able to determine exact weight at all positions of the head unit. This enables very accurate monitoring of the cervical muscles.

Details of the connection of the head station to the main frame and also the weight stack will now be described having reference to FIGS. 1, 5 and 6 of the drawings.

The upper end of the outer head unit 85 is secured to a circular plate 91 which is rotationally secured to an extension 4 of the main frame 3 of the apparatus. A releasable lock pin 93 having an upper end extension 94 fits up through the plate 91 into the frame extension 4 to lock the plate and the head station against rotation. When desired, the pin 93 is released to allow rotation of the head station. A pair of elongated grooves 95 are also provided in the plate and the pin can be fitted into one of the these grooves to allow a controlled rotation of the head station with the length of the grooves determining the range of rotation of the head station. The degree of rotation is picked up by the sensors and displayed at the visual display 13.

Both the rotation of the head station and the pivoting movement of the inner head brace relative to the outer head brace can be done without resistance by completely removing the pin 10 from the weight stack or under selected resistance according to the positioning of the pin in the weight stack. The cable connection to the head station is specifically designed to allow head station movement in both the backward and forward tilting and the side to side rotational directions.

Cable 11 runs from the weight stack and turns forward around a pulley 96 to a first pair of guide pulleys 97 outside of plate 91 and then to a second pair of guide pulleys 99 inside of the plate. The cable then passes downwardly around pulley 102 of a pair of balanced pulleys 101 to a pivot member 103 connected to frame member 36 of the inner head brace as best seen in FIGS. 5 and 6 of the drawings. The cable is then returned in an upward direction from a second pivot connector 105 again secured to frame member 36 of the inner head brace up to pulley 108 of a second pair of balanced pulleys 107. From here the cable proceeds forwardly to a further guide pulley 109 and finally onto a tensioning pulley 111. This tensioning pulley has a variable tension spring to offset the weight of the head station regardless of its position thereby increasing the accuracy of determining how much weight is being moved by the user.

The various cervical muscle controlled head movements achievable on the cervical apparatus will now be described having reference to FIGS. 8 through 14 of the drawings.

In FIG. 8, the user's head is fitted into the head station with the user sitting in an upright position on the seating unit. Straps 35 are placed over the user's shoulders to effectively immobilize the user's torso. This isolates movement of the head station to the use of the cervical muscles.

When sitting in the forward facing position of FIG. 8, the head station is fitted with pads 43 of FIG. 7. Frame piece 35 of the inner head brace can be set such that it is perfectly level horizontally or it can be tipped slightly rearwardly or forwardly by rotating frame piece 35 relative to frame piece 36 and locking it in the desired position using pin 42.

Figure 9:
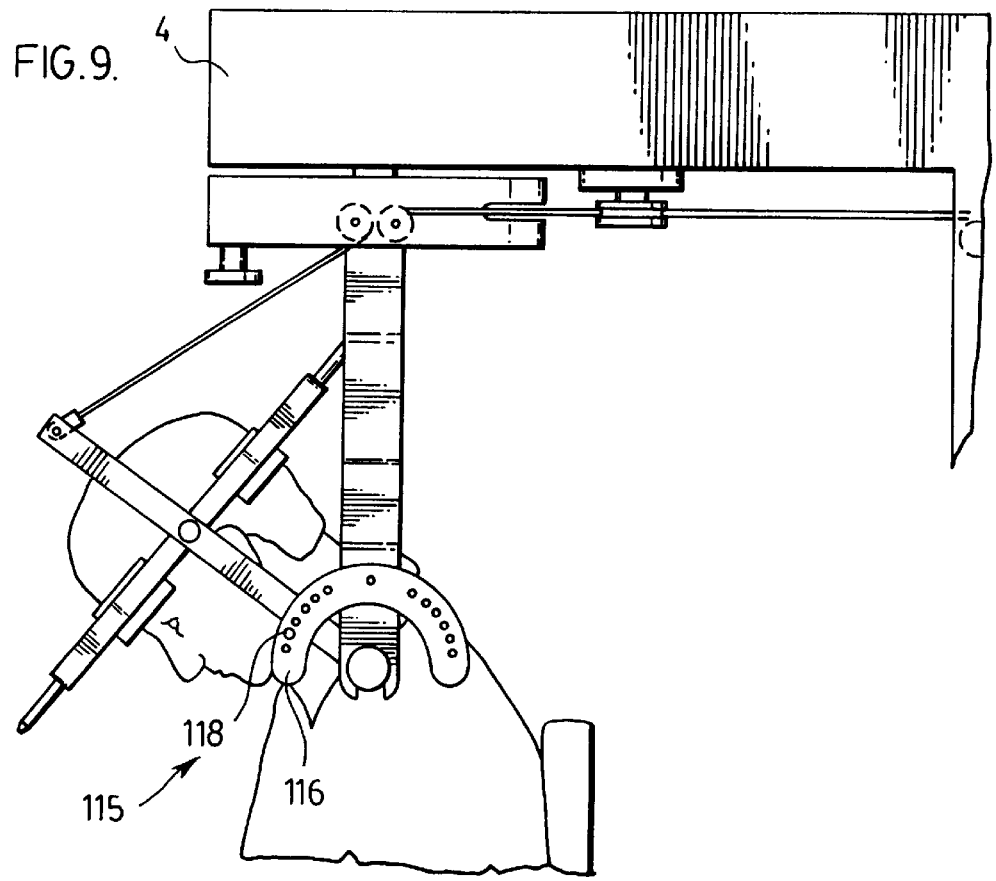

In order to evaluate flexion of the cervical muscles, lock pin 87 between the outer head unit and the inner head brace is removed and the user bends his or her neck forwardly causing the inner head brace to pivot forwardly as shown in FIG. 9 of the drawings. The amount of forward flexion can be determined through the provision of a range limiting assembly 115 in the form of an apertured plate 116 on the outer head unit and a pin 118 which extends between plate 116 and the inner head brace. If the pin is completely removed, then the inner head brace can be tipped forwardly as far as the user's neck can be bent or the pin can be placed such that it limits the range of motion of the inner head brace and the bending of the user's neck as shown in FIG. 9. This is of benefit for both evaluation of the cervical muscles and to prevent either injury or re-injury of the cervical muscles during training.

The pin 118 can also be fitted through plate 116 directly into the frame member 36 of the inner head brace locking it against movement.

Figure 3:
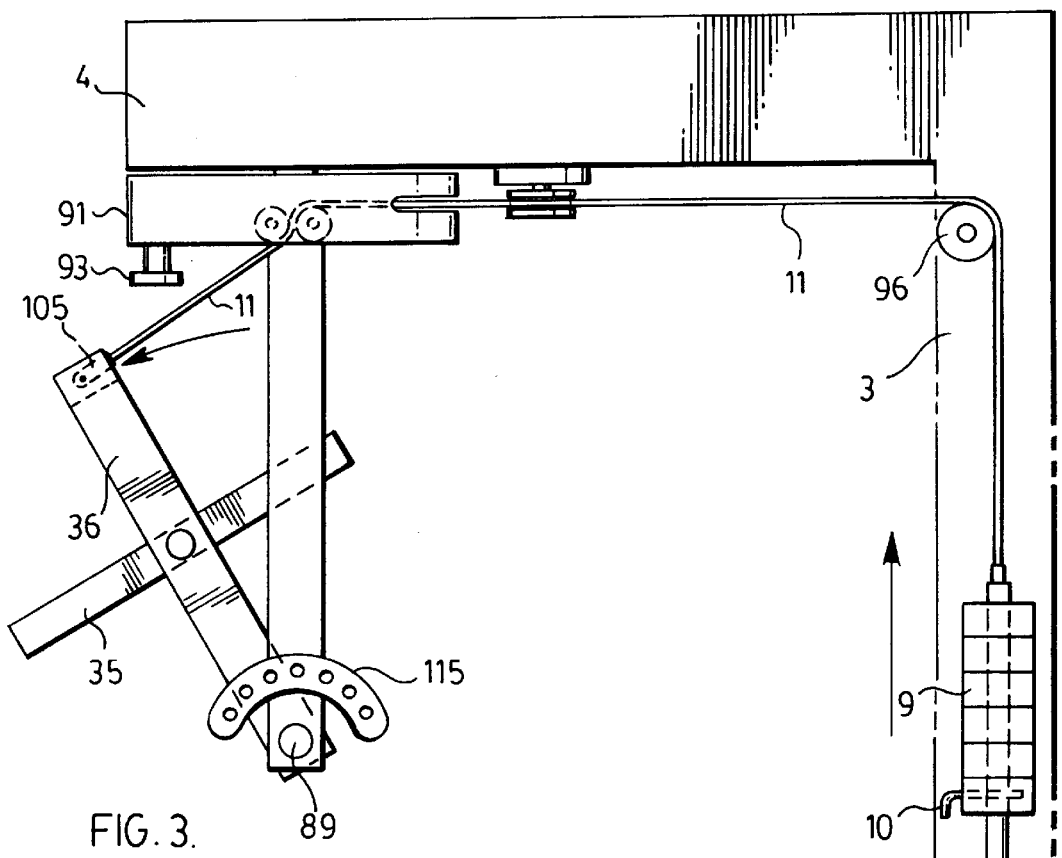
FIG. 3 is a side view of the head station and weight stack of the apparatus of FIG. 1.

The pivot connections 103 and 105 of the cable 11 to the upper end of the inner head brace allow upward pulling of the selected amount weight with the forward tipping of the head brace as shown in FIG. 3 of the drawings.

When the user's cervical muscles are evaluated or conditioned for cervical extension, the user simply bends his or her neck rearwardly in the opposite direction from that shown in FIG. 9.

It is to be understood that by releasing locking pin 93 between the outer head unit and the frame extension 4, the entire head unit can be turned from side to side by cervical rotation as shown in FIG. 12. As a result of the unique cable and pulley attachments to the head unit as earlier described, this rotation can also be achieved with selected resistance from the weight stack. Furthermore, cervical flexion and extension can be achieved simultaneously with cervical rotation. Both movements, i.e. the cervical rotation and the cervical flexion or extension will be monitored and separately displayed on the apparatus.

FIGS. 10 and 11 show the user in a position for lateral flexion of the cervical muscles. Here the seating unit has been turned at 90° from the FIG. 1 position and the head pads 43 of FIG. 7 have been replaced with the head pads 65 of FIG. 7c. Again, the inner head brace is free to pivot at the pivot connection 89 relative to the outer head unit. The range of motion limiter 115 can be set in a freely movable position by completely removing the pin or it can be set in a predetermined range limiting position by the pin.

As was the case with the cervical flexion, the lateral flexion can be achieved under a selected resistance from the weight stack.

Figure 13:
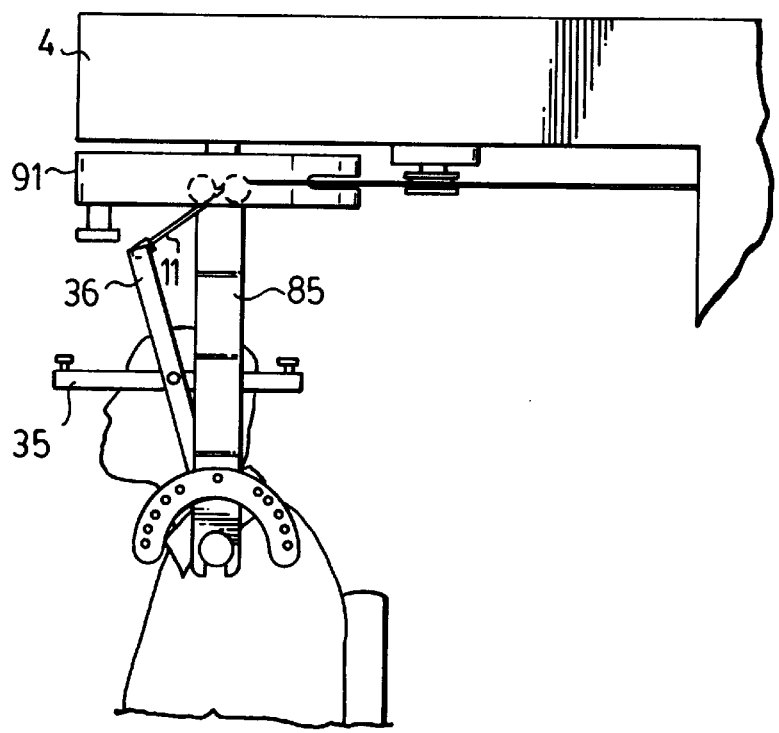
Figure 14:
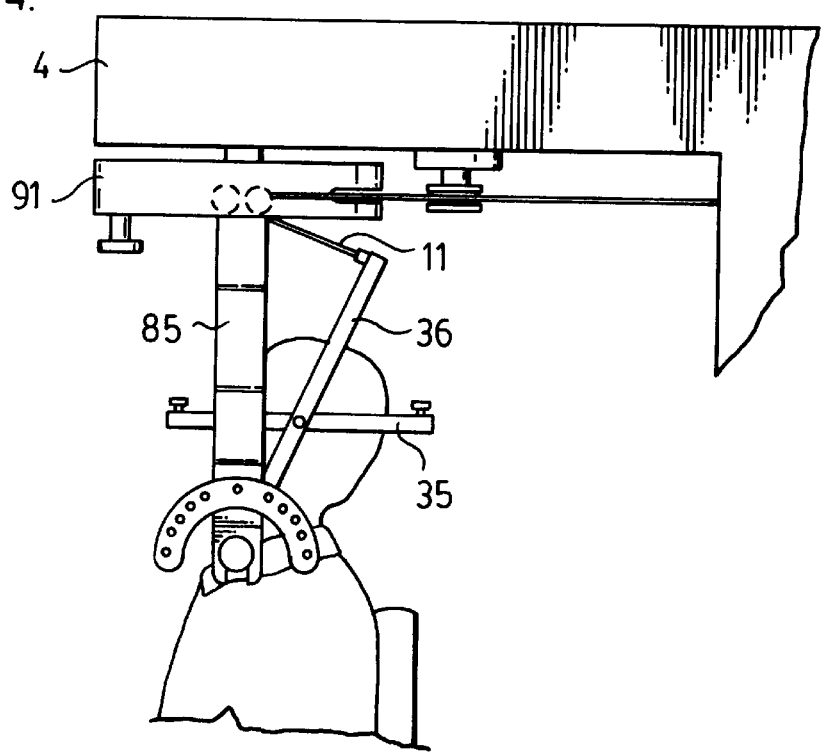

Other movements achievable with the apparatus are a protraction and retraction as shown in FIGS. 13 and 14 of the drawings. In order to allow these chin jutting out and chin jutting in movements, frame member 35 is allowed to pivot relative to frame member 36 of the inner head brace by releasing pin 42 from the rotational connection between pivot ends 37 and collar 38. Note by comparing FIGS. 13 and 14 with FIG. 3, that the frame members 35 and 36 of the inner head brace are movable to different angles relative to one another.

Figure 15:
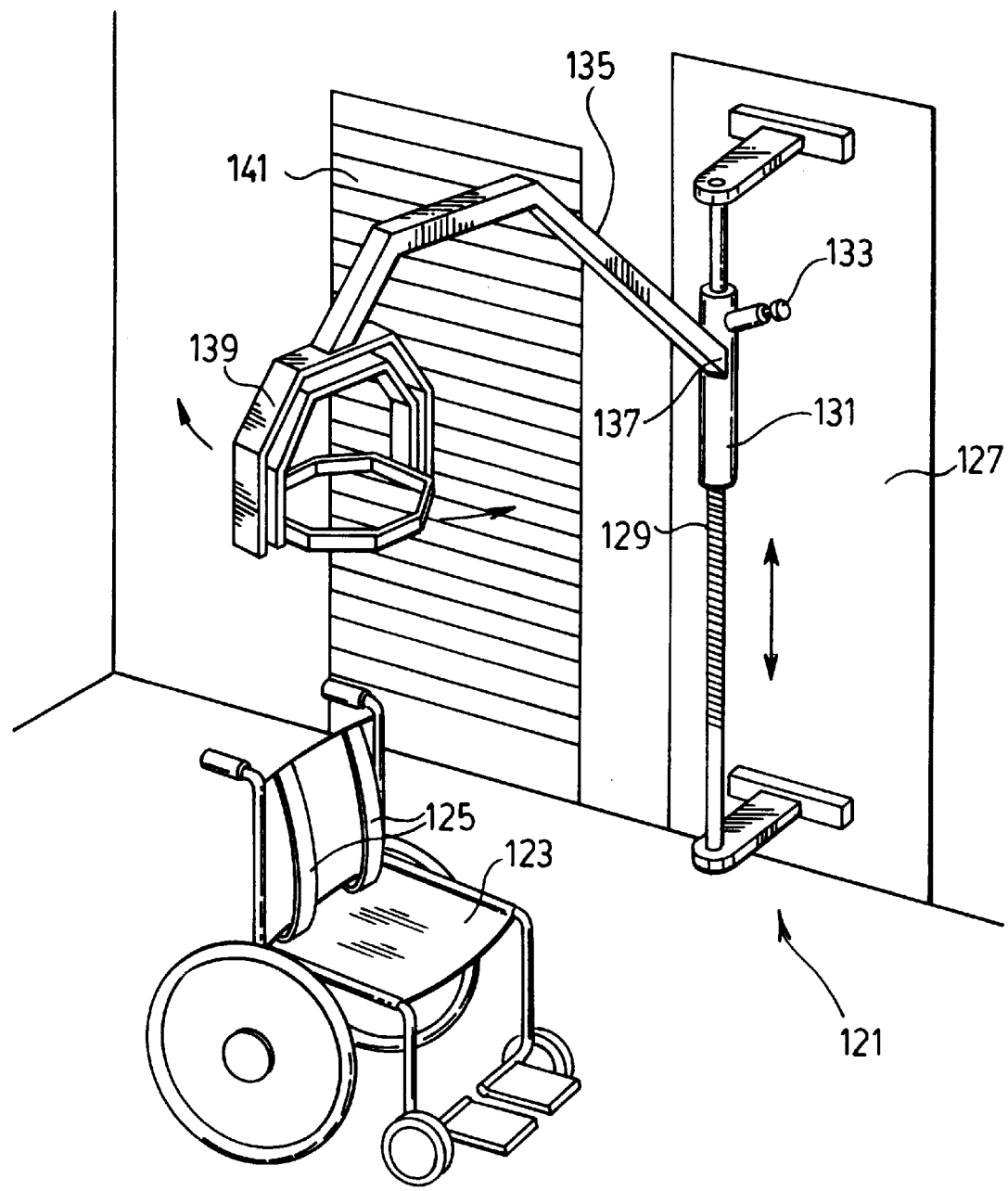
FIG. 15 is a perspective view of a cervical muscle evaluation and training apparatus according to a further preferred embodiment of the present invention.
Figure 16:
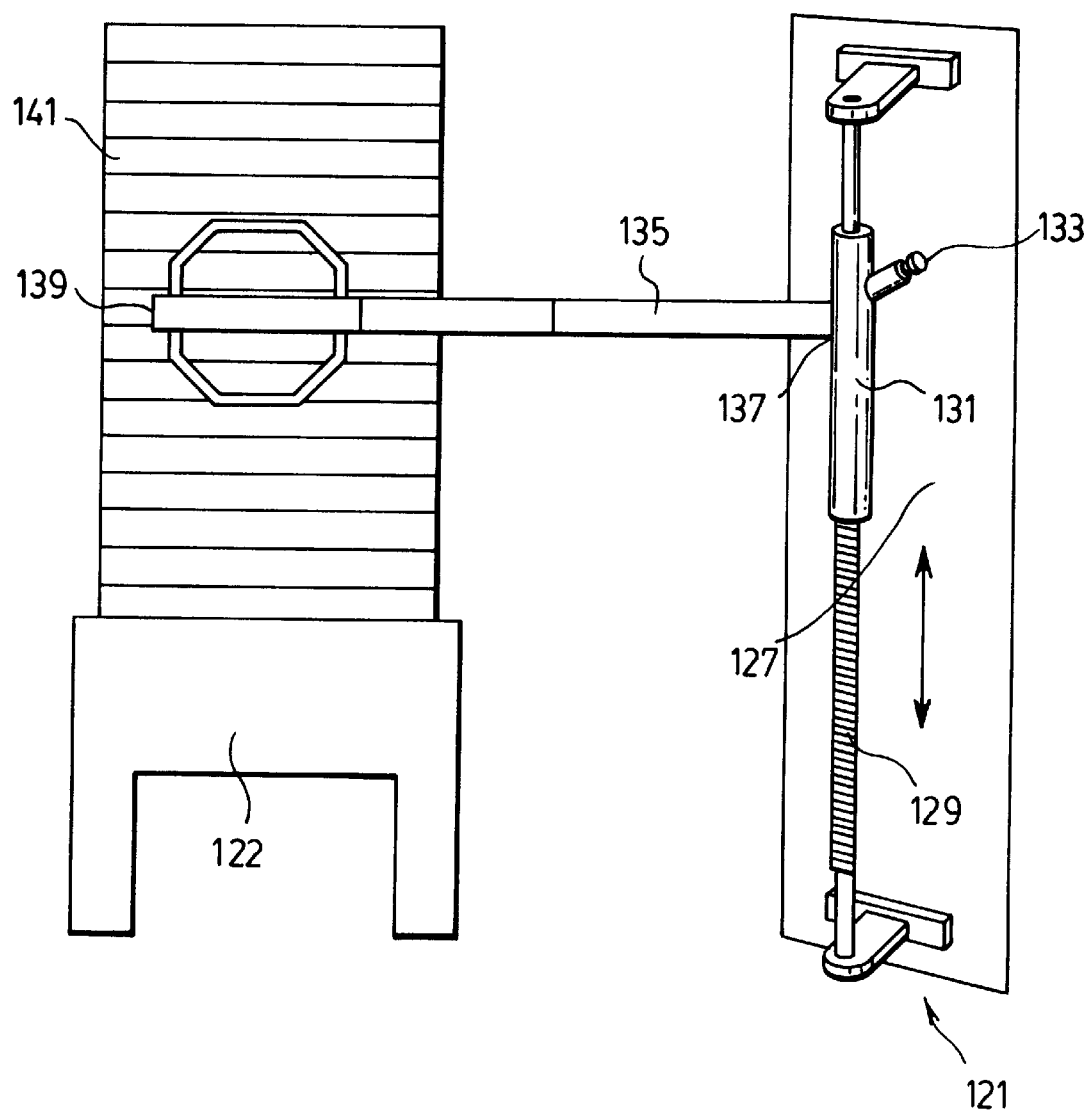
FIG. 16 shows an apparatus similar to that of FIG. 15 using an alternate body positioning unit.

The description above relates to the apparatus including the seating unit, head station and weight stack as all being mounted on a common frame. FIGS. 15 and 16 show modifications to the apparatus including body positioning units which are separate from but usable with other components of the apparatus. The two setups shown in FIGS. 15 and 16 are specifically designed for use by physically challenged persons.

FIG. 15 shows a cervical muscle evaluation and training apparatus generally indicated at 121. This apparatus is usable by a person on wheelchair 123 having shoulder straps 125.

Apparatus 121 includes a frame 127 which can be wall mounted or free standing. A sleeve 131 fits over a support rod 127 on the frame 127. Sleeve 131 is height adjustable on the rod by means of a releasable lock pin 133.

A head station 139 identical to the earlier described head station is pivotally suspended from an arm 135 which is in turn pivotally secured at 137 to height adjustable sleeve 131. Head station 139 is secured by cables and pulleys to a weight stack 141.

A person sitting in wheelchair 123 held by the shoulder straps 125 places his or her head directly beneath head station 139. Sleeve 131 is adjusted on support rod 129 such that the head station slides down over the head of the user. The head station is then appropriately adjusted to the size and shape of the user while sitting in the wheelchair to perform any of the various cervical controlled muscle head movements described in respect of FIGS. 8 through 14.

FIG. 16 shows apparatus 121 when used in association with a bed 122 to support the user in a supine position. In order to use apparatus 129 with the bed 122, arm 135 is swivelled 90° from the FIG. 15 position to appropriately locate head station 139 for receiving the user's head while lying on the bed. In addition, sleeve 131 will have to be moved on support 129 according to the height of the bed.

Although various preferred embodiments of the present invention have been described in detail, it will be appreciated by those skilled in the art, that variations may be made without departing from the spirit of the invention or the scope of the appended claims.

The embodiments of the invention in which an exclusive property or privilege is claimed are defined as follows:

1. Apparatus for cervical region evaluation and training, said apparatus comprising a support frame, a seating unit for seating a user of said apparatus in an upright position, a head unit above said seating unit, said head unit which is movable by cervical muscle controlled head movement of the user stabilized by said seating unit comprising an outer head station mounted to said support frame, and an inner head brace comprising a first frame piece mounted to pivot about a first horizontal axis relative to said outer head station and a second frame piece mounted to rotate about a second horizontal axis relative to said first frame piece, said second frame piece being provided with head receiving means adjustable to different head sizes and shapes, and monitoring means for monitoring movement of said head unit, said seating unit being rotatable to different positions of upright seating below said head unit to vary the cervical region muscles used in moving said head unit.

2. Apparatus as claimed in claim 1, including releasable locking means which when in a locking position locks said inner head brace from pivoting on said outer head station.

3. Apparatus as claimed in claim 1, including releasable locking means which when in a locking position limits range of pivot motion of said inner head brace relative to said outer head station.

4. Apparatus as claimed in claim 3, wherein said releasable locking means is adjustable to adjust the limit of range of pivot motion of said inner head brace.

5. Apparatus as claimed in claim 1, wherein said outer head station is rotatable about a vertical axis of said apparatus.

6. Apparatus as claimed in claim 5, including releasable locking means which when in a locking position limits range rotation of said outer head station.

7. Apparatus as claimed in claim 6, wherein said releasable locking means is adjustable in position to adjust the range of rotation of said outer head station.

* * * * *